United States Patent
Morrow et al.

(10) Patent No.: US 6,485,935 B1
(45) Date of Patent: Nov. 26, 2002

(54) STRUCTURE OF THE ANKYRIN BINDING DOMAIN OF A α-NA, K-ATPASE

(75) Inventors: Jon S. Morrow, Madison; Prasad Devarajan, New Haven; Zhushan Zhang, Hamden, all of CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/480,675

(22) Filed: Jan. 11, 2000

Related U.S. Application Data

(63) Continuation of application No. PCT/US98/14836, filed on Jul. 17, 1998.
(60) Provisional application No. 60/053,218, filed on Jul. 18, 1997.

(51) Int. Cl.[7] .......................... C12P 21/06; C12P 21/02; C12N 9/02; C07K 1/00; C07H 21/04
(52) U.S. Cl. ..................... 435/69.1; 435/69.7; 435/189; 435/193; 435/212; 435/252.3; 435/320.1; 536/23.1; 536/23.2; 530/362; 530/364; 530/328; 530/330
(58) Field of Search .............................. 435/69.1, 252.3, 435/320.1, 193, 212, 69.7; 536/23.1, 23.2; 530/362, 364, 328, 330

(56) References Cited

PUBLICATIONS

Sequence Alignments : Applicants Seq ID Nos : 1–2 and Canessa ' accession 20970.*
Beck et al., Golgi membrane skeleton: identification, localization and oligomerization of a 195 kDa ankyrin isoform associated with the Golgi complex, J. Cell Sci. 110:1239–1249 (1997).
Bennett, Ankyrins —adaptors between diverse plasma membrane proteins and the cytoplasm, J. Biol. Chem. 267:8703–8706 (1992).
Canessa et al., Mutation of a cysteine in the first transmembrane segment of a Na, K– ATPase alpha subunit confers ouabain resistance, EMBO J. 11:1681–1687 (1992).
Davis et al., Ankyrin–binding proteins related to nervous system cell adhesion molecules: candidates to provide transmembrane and intercellular connections in adult brain, J. Cell Biol. 121:121–133 (1993).
Devarajan et al., Identification of a small cytoplasmic ankyrin ($Ank_{G119}$) in the kidney and muscle that binds βIE spectrin and associates with the golgi apparatus, J. Cell Biol. 133:819–830 (1996).
Devarajan et al., Ankyrin binding is required for Er to golgi trafficking and plasma membrane assembly of Na,K–ATPase, Molec. Biol. Cell. 8(supp):305a, Abstract No. 1769 (1997).
Devarajan et al., Na,K–ATPase transport from endoplasmic reticulum to golgi requires the golgi spectrin–ankyrin G119 skeleton in madin darby canine kidney cells, Proc. Natl. Acad. Sci. USA 94:10711–10716 (1997).

Devarajan et al., Ankyrin binds to two distinct cytoplasmic domains of Na,K–ATPase α subunit, Proc. Natl. Acac. Sci. USA 91:2965–2969 (1994).
Diederich et al., Cytosolic interaction between deltex and notch ankyrin repeats implicates deltex in the notch signaling pathway, Development 120:473–481 (1994).
Ferrante et al., Shark, a Src homology 2, ankyrin repeat, tyrosin kinase, is expressed on the apical surfaces of ectodermal epithelia, Proc. Natl. Acad. Sci. USA 92:1911–1915 (1995).
Godi et al., ADP ribosylation factor regulates spectrin binding to the golgi complex, Proc. Natl. Acad. Sci. USA 95:8607–8612 (1998).
Gorina et al., Structure of the p53 tumor suppressor bound to the ankyrin and SH3 domains of 53BP2, Science 274:1001–1005 (1996).
Gundersen et al., Apical polarity of Na,K–ATPase in retinal pigment epithelium is linked to a reversal of the ankyrin–fodrin submembrane cytoskeleton, J. Cell Biol. 112:863–872 (1991).
Inoue et al., Bcl–3, a member of the IκB proteins, has distinct specificity towards the Rel family of proteins, Oncogene 8:2067–2073 (1993).
Jordan et al., Identification of a binding motif for ankyrin on the α–subunit of $Na^+,K^+$–ATPase, J. Biol. Chem. 270:29971–29975 (1995).
Kerr et al., Signal transduction: the nuclear target, Curr. Opin. Cell Biol. 4:496–501 (1992).
Léveillard et al., Diverse molecular mechanisms of inhibition of NF–κB/DNA binding complexes by IκB proteins, Gene Expr. 3:135–150 (1993).
Lokeshwar et al., Akyrin–binding domain of CD44(GP85) is required for the expression of hyaluronic acid–mediated adhesion function, J. Cell Biol. 126:1099–1109 (1994).
Luna et al., Cytoskeleton–plasma membrane interactions, Science 258:955–964 (1992).
Michaely et al., The membrane–binding domain of ankyrin contains four independently folded subdomains, each comprised of six ankyrin repeats, J. Biol. Chem. 268:22703–22709 (1993).
Morrow et al., Ankyrin links fodrin to the alpha subunit of Na, K–ATPase in madin–darby canine kidney cells and in intact renal tubule cells, J. Cell Biol. 108:455–465 (1989).
Nelson et al., Involvement of the membrane–cytoskeleton in development of epithelial cell polarity, Seminars in Cell Biology 1:359–371 (1990).
Smith et al., Gastric parietal cell $H^+$–$K^+$–ATPase microsomes are associated with isoforms of ankyrin and spectrin, Am. J. Physiol. 264:C63–70 (1993).
Shull et al., Molecular cloning of the rat stomach ($H^+$+$K^+$)–ATPase, J. Biol. Chem. 261:16788–16791 (1986).

* cited by examiner

Primary Examiner—Tekchand Saldha
(74) Attorney, Agent, or Firm—Morgan, Lewis & Bockius LLP

(57) ABSTRACT

The present invention provides a polypeptide of 26 amino acid residues that comprises the minimal ankyrin binding (MAB) domain. The MAB domain is responsible for the interactions between a Na,K-ATPase and ankyrin. The present invention also provides the three dimensional structure of the MAB domain. Also provided by the present invention are methods for modulating the interaction of a Na,K-ATPase and ankyrin.

18 Claims, 6 Drawing Sheets

A MSPILGYWKIKGLVQPTRLLLEYLEEKYEEHLYERDEGDK
WRNKKFELGLEFPNLPYYIDGDVKLTQSMAIIRYIADKHN
MLGGCPKERAEISMLEGAVLDIRYGVSRIAYSKDFETLKV  GST
DFLSKLPEMLKMFEDRLCHKTYLNGDHVTHPDFMLYDALD
VVLYMDPMCLDAFPKLVCFKKRIEAIPQIDKYLKSSKYIA
WPLQGWQATFGGGDHPPKSD-

-lvprgsSYYQEAKSSKIMESFKNMVPQQALVnss  MABD
       |                         |  Na,K-ATPase
      142                 166

A

| | S | Y | Y | Q | E | A | K | S | S | K | I | M | E | S | F | K | N | M | V | P | Q | Q | A | L | V |
|---|---|---|---|---|---|---|---|---|---|---|---|---|---|---|---|---|---|---|---|---|---|---|---|---|---|
| Human a1 | S | Y | Y | Q | E | A | K | S | S | K | I | M | E | S | F | K | N | M | V | P | Q | Q | A | L | V |
| Human a2 | - | - | - | - | - | - | - | - | - | - | - | - | D | - | - | - | - | - | - | - | - | - | - | - | - |
| Human a3 | - | - | - | - | - | - | - | - | - | - | - | - | - | - | - | - | - | - | - | - | - | - | - | - | - |
| Rat a1 | - | - | - | - | - | - | - | - | - | - | - | - | - | - | - | - | - | - | - | - | - | - | - | - | - |
| Dog a1 | - | - | - | - | - | - | - | - | - | - | - | - | - | - | - | - | - | - | - | - | - | - | - | - | - |
| Pig a1 | - | - | - | - | - | - | - | - | - | - | - | - | - | - | - | - | - | - | - | - | - | - | - | - | - |
| Xenopus a1 | - | - | - | - | - | - | - | - | - | - | - | - | - | - | - | - | - | - | - | - | - | - | - | - | - |
| Torpedo a1 | - | - | - | - | - | - | - | - | - | - | - | - | D | - | - | - | - | - | - | - | - | - | - | - | - |
| Drosophila a1 | - | - | - | - | - | S | - | - | - | - | - | - | - | - | - | - | - | - | - | - | - | - | F | - | T | - |
| Caenorhabditis a1 | Q | - | - | - | - | S | - | - | - | - | - | - | D | - | - | - | - | - | - | - | T | F | - | - | - |
| Hum renal H/K-ATPase | A | - | - | - | - | - | - | - | T | N | - | - | S | - | - | N | K | - | I | - | - | - | - | - | - |
| Hum gastric H/K-ATPase | G | - | - | - | - | F | - | - | T | N | - | I | A | - | - | - | - | L | - | - | - | - | - | T | - |

Figure 4A

SEQUENCE LISTING

<160> NUMBER OF SEQ ID NOS: 17

<210> SEQ ID NO 1
<211> LENGTH: 7
<212> TYPE: PRT
<213> ORGANISM: Homo sapiens
<220> FEATURE:
<221> NAME/KEY: misc_feature
<222> LOCATION: ()..()
<223> OTHER INFORMATION: Alpha Na,K-ATP ase, amino acids 152-158

<400> SEQUENCE: 1

Met Glu Ser Phe Lys Asn Met
1               5

<210> SEQ ID NO 2
<211> LENGTH: 25
<212> TYPE: PRT
<213> ORGANISM: Homo sapiens
<220> FEATURE:
<221> NAME/KEY: misc_feature
<222> LOCATION: ()..()
<223> OTHER INFORMATION: Alpha Na,K-ATPase, amino acids 142-166 of
      ankyrin binding domain

<400> SEQUENCE: 2

Ser Tyr Tyr Gln Glu Ala Lys Ser Ser Lys Ile Met Glu Ser Phe Lys
1               5                   10                  15

Asn Met Val Pro Gln Gln Ala Leu Val
            20                  25

<210> SEQ ID NO 3
<211> LENGTH: 7
<212> TYPE: PRT
<213> ORGANISM: Artificial Sequence
<220> FEATURE:
<223> OTHER INFORMATION: Description of Arificial Sequence:  Amphipathic
      loop of Alpha Na,K-ATPase minimal ankyrin biding domain
<221> NAME/KEY: VARIANT
<222> LOCATION: (1)..(7)
<223> OTHER INFORMATION: X at position 1 = Met or Ile; X at position 2 =
      Glu, Asp or Ser; X at positions 5 and 6 = Lys or Asn; X at
      position 7 = Met or Leu.

<400> SEQUENCE: 3

Xaa Xaa Ser Phe Xaa Xaa Xaa
1               5

<210> SEQ ID NO 4
<211> LENGTH: 220
<212> TYPE: PRT
<213> ORGANISM: Schistosoma japonicum
<220> FEATURE:
<221> NAME/KEY: misc_feature

```
<222> LOCATION: ()..()
<223> OTHER INFORMATION: Glutathione S-transferase

<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp
    210                 215                 220

<210> SEQ ID NO 5
<211> LENGTH: 34
<212> TYPE: PRT
<213> ORGANISM: Homo sapiens
<220> FEATURE:
<221> NAME/KEY: BINDING
<222> LOCATION: (7)..(31)
<223> OTHER INFORMATION: Minimal ankyrin binding domain of Na,K-ATPase

<400> SEQUENCE: 5

Leu Val Pro Arg Gly Ser Ser Tyr Tyr Gln Glu Ala Lys Ser Ser Lys
1               5                   10                  15

Ile Met Glu Ser Phe Lys Asn Met Val Pro Gln Gln Ala Leu Val Asn
            20                  25                  30

Ser Ser

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Ankyrin
      binding motif

<400> SEQUENCE: 6

Ala Leu Leu Lys
```

1

<210> SEQ ID NO 7
<211> LENGTH: 25
<212> TYPE: PRT
<213> ORGANISM: Homo sapiens
<220> FEATURE:
<221> NAME/KEY: VARIANT
<222> LOCATION: (13)..(13)
<223> OTHER INFORMATION: Alpha 2 variant of minimal ankyrin binding
      domain

<400> SEQUENCE: 7

Ser Tyr Tyr Gln Glu Ala Lys Ser Ser Lys Ile Met Asp Ser Phe Lys
1               5                   10                  15

Asn Met Val Pro Gln Gln Ala Leu Val
            20                  25

<210> SEQ ID NO 8
<211> LENGTH: 25
<212> TYPE: PRT
<213> ORGANISM: Homo sapiens
<220> FEATURE:
<221> NAME/KEY: misc_feature
<222> LOCATION: ()..()
<223> OTHER INFORMATION: Alpha 3 variant of minimal ankyrin binding
      domain

<400> SEQUENCE: 8

Ser Tyr Tyr Gln Glu Ala Lys Ser Ser Lys Ile Met Glu Ser Phe Lys
1               5                   10                  15

Asn Met Val Pro Gln Gln Ala Leu Val
            20                  25

<210> SEQ ID NO 9
<211> LENGTH: 25
<212> TYPE: PRT
<213> ORGANISM: Rattus rattus
<220> FEATURE:
<221> NAME/KEY: misc_feature
<222> LOCATION: ()..()
<223> OTHER INFORMATION: Minimal ankyrin binding domain

<400> SEQUENCE: 9

Ser Tyr Tyr Gln Glu Ala Lys Ser Ser Lys Ile Met Glu Ser Phe Lys
1               5                   10                  15

Asn Met Val Pro Gln Gln Ala Leu Val
            20                  25

<210> SEQ ID NO 10
<211> LENGTH: 25
<212> TYPE: PRT
<213> ORGANISM: Canis familiaris
<220> FEATURE:
<221> NAME/KEY: misc_feature
<222> LOCATION: ()..()
<223> OTHER INFORMATION: Minimal ankyrin binding domain

<400> SEQUENCE: 10

Ser Tyr Tyr Gln Glu Ala Lys Ser Ser Lys Ile Met Glu Ser Phe Lys
1               5                   10                  15

Asn Met Val Pro Gln Gln Ala Leu Val
            20                  25

<210> SEQ ID NO 11
<211> LENGTH: 25

```
<212> TYPE: PRT
<213> ORGANISM: Sus scrofa
<220> FEATURE:
<221> NAME/KEY: misc_feature
<222> LOCATION: ()..()
<223> OTHER INFORMATION: Minimal ankyrin binding domain

<400> SEQUENCE: 11

Ser Tyr Tyr Gln Glu Ala Lys Ser Ser Lys Ile Met Glu Ser Phe Lys
1               5                   10                  15

Asn Met Val Pro Gln Gln Ala Leu Val
            20                  25

<210> SEQ ID NO 12
<211> LENGTH: 25
<212> TYPE: PRT
<213> ORGANISM: Xenopus laevis
<220> FEATURE:
<221> NAME/KEY: misc_feature
<222> LOCATION: ()..()
<223> OTHER INFORMATION: Minimal ankyrin binding domain

<400> SEQUENCE: 12

Ser Tyr Tyr Gln Glu Ala Lys Ser Ser Lys Ile Met Glu Ser Phe Lys
1               5                   10                  15

Asn Met Val Pro Gln Gln Ala Leu Val
            20                  25

<210> SEQ ID NO 13
<211> LENGTH: 25
<212> TYPE: PRT
<213> ORGANISM: Torpedo californica
<220> FEATURE:
<221> NAME/KEY: misc_feature
<222> LOCATION: ()..()
<223> OTHER INFORMATION: Minimal ankyrin binding domain

<400> SEQUENCE: 13

Ser Tyr Tyr Gln Glu Ala Lys Ser Ser Lys Ile Met Asp Ser Phe Lys
1               5                   10                  15

Asn Met Val Pro Gln Gln Ala Leu Val
            20                  25

<210> SEQ ID NO 14
<211> LENGTH: 25
<212> TYPE: PRT
<213> ORGANISM: Drosophila melanogaster
<220> FEATURE:
<221> NAME/KEY: misc_feature
<222> LOCATION: ()..()
<223> OTHER INFORMATION: Minimal ankyrin binding domain

<400> SEQUENCE: 14

Ser Tyr Tyr Gln Glu Ser Lys Ser Ser Lys Ile Met Glu Ser Phe Lys
1               5                   10                  15

Asn Met Val Pro Gln Phe Ala Thr Val
            20                  25

<210> SEQ ID NO 15
<211> LENGTH: 25
<212> TYPE: PRT
<213> ORGANISM: Caenorhabditis elegans
<220> FEATURE:
<221> NAME/KEY: misc_feature
<222> LOCATION: ()..()
<223> OTHER INFORMATION: Minimal ankyrin binding domain
```

```
<400> SEQUENCE: 15

Gln Tyr Tyr Gln Glu Ser Lys Ser Lys Ile Met Asp Ser Phe Lys
1               5                   10                  15

Asn Met Val Pro Thr Phe Ala Leu Val
            20                  25

<210> SEQ ID NO 16
<211> LENGTH: 25
<212> TYPE: PRT
<213> ORGANISM: Homo sapiens
<220> FEATURE:
<221> NAME/KEY: misc_feature
<222> LOCATION: ()..()
<223> OTHER INFORMATION: Minimal ankyrin binding domain of renal
      H/K-ATPase

<400> SEQUENCE: 16

Ala Tyr Tyr Gln Glu Ala Lys Ser Thr Asn Ile Met Ser Ser Phe Asn
1               5                   10                  15

Lys Met Ile Pro Gln Gln Ala Leu Val
            20                  25

<210> SEQ ID NO 17
<211> LENGTH: 25
<212> TYPE: PRT
<213> ORGANISM: Homo sapiens
<220> FEATURE:
<221> NAME/KEY: misc_feature
<222> LOCATION: ()..()
<223> OTHER INFORMATION: Minimal ankyrin binding domain of gastric
      H/K-ATPase

<400> SEQUENCE: 17

Gly Tyr Tyr Gln Glu Phe Lys Ser Thr Asn Ile Ile Ala Ser Phe Lys
1               5                   10                  15

Asn Leu Val Pro Gln Gln Ala Thr Val
            20                  25
```

STRUCTURE OF THE ANKYRIN BINDING DOMAIN OF A α-NA, K-ATPASE

RELATED APPLICATIONS

This application is a continuation of PCT/US98/14836 (filed Jul. 17, 1998), which claims the benefit of U.S. Provisional Application No. 60/053,218 (filed Jul. 18, 1997), both of which are herein incorporated by reference in their entirety.

TECHNICAL FIELD

The present invention relates to the identification of the minimal ankyrin binding domain (MAB) responsible for the interactions between a Na,K-ATPase and ankyrin. The present invention also relates to a method of determining the minimal ankyrin binding domain and its three dimensional structure in other integral membrane proteins that associate or bind to ankyrin through the use of deletion analysis and carrier mediated crystallization.

Another aspect of the present invention relates to a method of screening for compounds, including small peptides or peptide analogs, that inhibit, promote or modulate the interaction of a Na,K-ATPase and ankyrin. Lastly, the present invention relates to a method of inhibiting, promoting or modulating the interaction between a Na,K-ATPase and ankyrin in the presence of a compound, including small peptides or peptide analogs, that inhibits, enhances or modulates the interaction between a Na,K-ATPase and a

BACKGROUND OF THE INVENTION

Tethering interactions between the cytoplasmic domains of integral membrane proteins and other macromolecules, mediated by ankyrin or proteins containing ankyrin-like repeat structures, play fundamental roles in diverse biological activities including growth and development (1, 2, 3, 4, 5), protein trafficking (6, 7, 8, 9), the establishment and maintenance of cellular polarity (10, 11, 12, 13), cell adhesion (14, 15), signal transduction (2, 16, 17, 18, 19, 20), and mRNA transcription (21, 22). Ankyrin, including its many isoforms (reviewed in 23, 24), is also the most ubiquitous adapter protein mediating linkage of membrane proteins with the spectrin-based skeleton, both at the plasma membrane (reviewed in (25, 26) as well as with internal membrane compartments including the Golgi apparatus (6, 7, 8). A characteristic feature of most ankyrins is the presence of a variable number of well conserved 33-residue repetitive units (ankyrin repeats) that individually or in combination bind specifically a large repertoire of transmembrane proteins (reviewed in 24). Since no data on the structure of a ankyrin binding domain in an integral membrane protein exists, there is little understanding of how such broad but specific binding capacity is achieved, or of how so many different membrane proteins can interact with a single ankyrin molecule (27, 28).

The α-subunit of Na,K-ATPase interacts specifically with ankyrin (12, 29). This interaction is required for the stabilization of Na,K-ATPase at the basolateral plasma membrane of epithelial cells, and for the transport of NaK-ATPase from the endoplasmic reticulum to the Golgi apparatus (8). Distinct regions of both cytoplasmic domains II and III of α-Na,K-ATPase bind ankyrin in vitro. These sequences appear to act independently, and those in cytoplasmic domain II (residues 140–290) account for most of α-Na,K-ATPase's affinity for ankyrin (29, 30).

SUMMARY OF THE INVENTION

The present inventors have for the first time discovered the threedimensional structure of the minimal ankyrin binding domain of a integral membrane protein that binds to ankyrin. The present invention is based on the inventors' discovery that an ankyrin 33 residue repeating motif, an L-shaped structure with protruding β-hairpin tips, mediates specific macromolecular interactions in cytoskeletal, membrane and regulatory proteins. The association between ankyrin and α-Na,K-ATPase, a ubiquitous membrane protein critical to vectorial transport of ions and nutrients, is required to assemble and stabilize Na,K-ATPase at the membrane. α-Na,K-ATPase binds both red cell (ANK1) and Madin Darby Canine Kidney (MDCK) cell ankyrin (ANK3) predominately by residues 142–166, located within its second putative cytoplasmic domain. Fusion peptides of glutathione-S-transferase incorporating these residues bind specifically to ankyrin. The three-dimensional structure (2.6 Å) of this minimal ankyrin-binding motif fusion peptide reveals a 7 residue loop with one charged hydrophilic face capping a double β-strand. Comparison of this structure with putative ankyrin binding sequences in p53, CD44, neurofascin/LI, and the IP3-receptor suggests that the versatility and specificity of ankyrin binding to its ligands is achieved by interactions involving the β-hairpin tips of the ankyrin repeats with 5–7 residue loops presented at the surface of other such macromolecules.

BRIEF DESCRIPTION OF THE DRAWINGS

FIG. 1A–FIG. 1B presents the:

(A) Schematic representation of the five cytoplasmic domains of α-Na,K-ATPase and their relationship to the ankyrin binding peptide sequences identified here. Codon positions defining each peptide are shown.

(B) Each depicted peptide was prepared as a fusion construct with GST, and examined for its ability to bind either purified ANK1 (from human red cells) or MDCK cell kidney ankyrin (ANK3) derived from whole MDCK cell lysates.

FIG. 2A represents the primary structure of the GST-MAB fusion peptide. The GST sequence (SEQ ID NO: 4) is shown on top, followed by the MAB sequence (SEQ ID NO: 5). Residues in lower case represent the linker sequences joining MAB to GST. FIG. 2B represents the three-dimensional structure of the GST-MAB peptide.

FIG. 3A–FIG. 3F represents three-axis views of the structure of the minimal ankyrin binding domain of α-Na, K-ATPase.

Figure 4B:
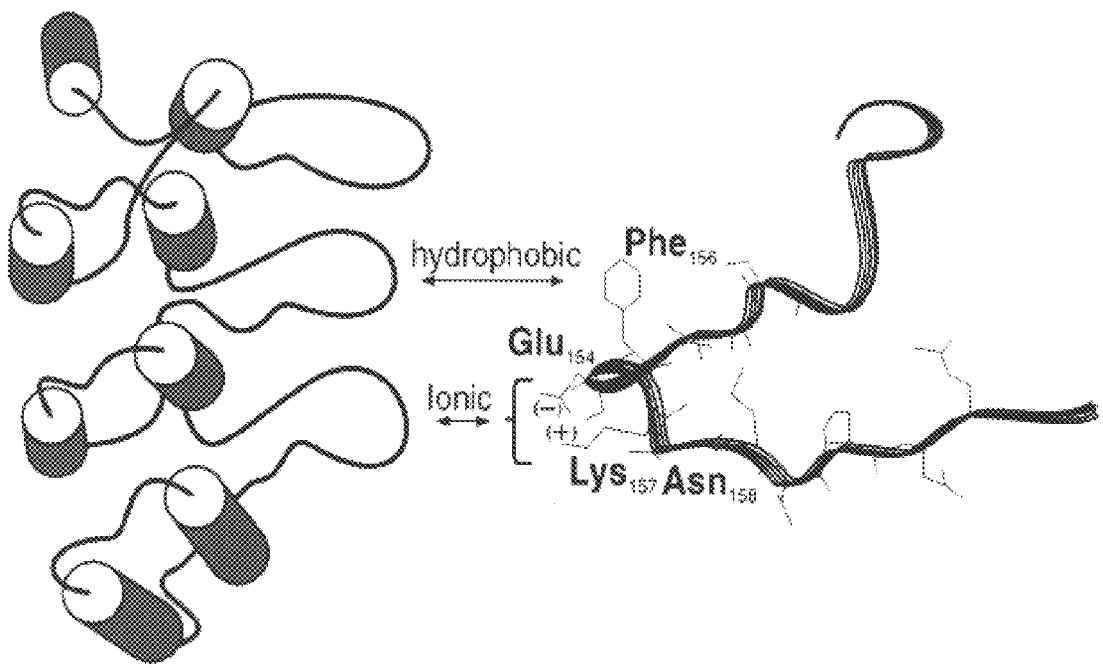

FIG. 4A–FIG. 4B: FIG. 4A: Sequence alignment of the minimal ankyrin binding domain (peptide IIA) with other proteins found in GenBank and Swiss-Prot (SEQ ID NOS: 2 and 7–17, from top to bottom, respectively) Dashes represent residues identical to human Na,K-ATPase α1 subunit, residues 142–166. FIG. 4B represents a model of how Na,K-ATPases may interact with one or more ankyrin repeat units.

Figure 5:
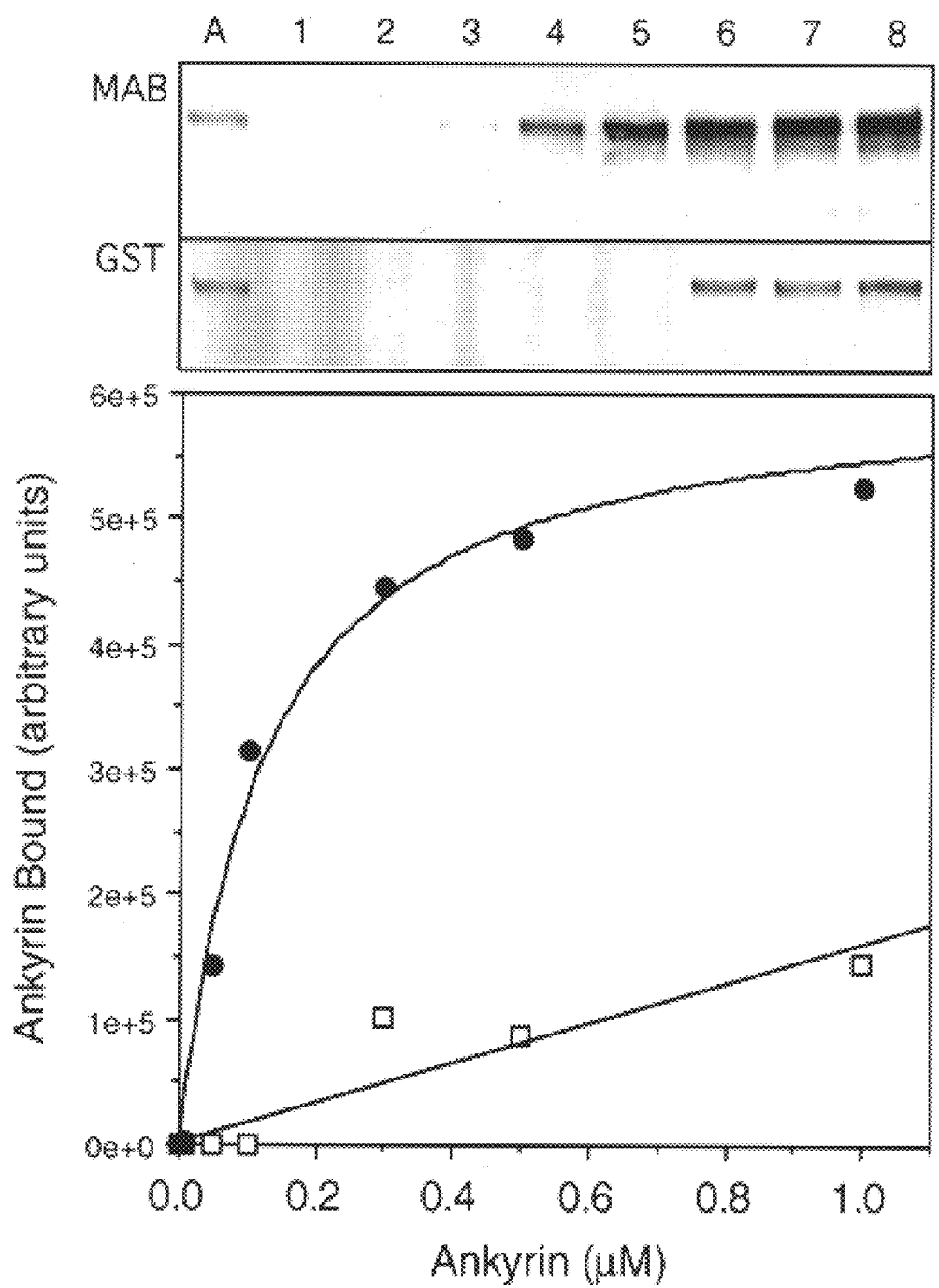

FIG. 5 shows that GST-MAB binds ankyrin with high affinity. (top) Purified $Ank_R$ was biotinylated, and incubated with GST-MAB (peptide IIa) or GST. Lane A, purified biotinylated ankyrin (30 ng); lanes 1 to 8 respectively, 0.001, 0.005, 0.01, 0.05, 0.1, 0.3, 0.5, and 1.0 μM ankyrin. Shown are the autofluorograms of the bound fractions for either GST-MAB or GST alone. (bottom) The ankyrin in the GST-MAB (●) or GST (□) bound fractions as a function of the ankyrin concentration. Regression analysis yielded an estimated Kd=118±50 nM and a $B_{max\_}=6.1±0.7×10^5$ (arbitrary units).

MODES OF CARRYING OUT THE INVENTION
General Description

The present invention relates to the identification of the minimal ankyrin binding domain (MAB) responsible for the interactions between a Na,K-ATPase and ankyrin. The MAB from Na,K-ATPase, including the α-Na,K-ATPase, in peptide form can be used as a peptide inhibitor to block the interaction between the Na,K-ATPase and ankyrin, thereby blocking the transport of the Na,K-ATPase to the plasma membrane. The use of a peptide inhibitor or analog to block the interaction of a Na,K-ATPASE and ankyrin may be indicated for the treatment of conditions in which the abnormal levels of the Na,K-ATPase contribute to the condition.

The peptides of the present invention include variants of the peptide defined as the MAB for a specific protein, including the MAB from α-NaK-ATPase. These variants differ in sequence from the MAB but still retain the ability to bind to ankyrin and to modulate the binding of the specific protein to ankyrin. For instance, amino acid substitutions can be made in naturally occurring MAB peptide sequences with amino acids with similar side chains (conservative substitutions). Conservative amino acid substitutions refer to substitutions in the amino acid sequence of a naturally occurring MAB with amino acids having similar side chains. Examples of amino acids having similar side chains include: amino acids having aliphatic side chains such as glycine, alanine, valine, leucine, and isoleucine; amino acids having aliphatic-hydroxyl side chains such as serine and threonine; amino acids having amide-containing side chains such as asparagine and glutamine; amino acids having aromatic side chains such as phenylalanine, tyrosine, and tryptophan; amino acids having basic side chains such as lysine, arginine, and histidine; amino acids having sulfur-containing side chains such as cysteine and methionine. Preferred conservative amino acids substitutions are: valine-leucine-isoleucine, phenylalanine-tyrosine, lysine-arginine, alanine-valine and asparagine-glutamine.

The term "naturally-occurring" as used herein as applied to a peptide refers to the fact that the peptide sequence can be found in nature. For example, a polypeptide sequence that is present in an organism and can be isolated from a source in nature and which has not modified by man.

An example of a variant of the naturally occurring peptide corresponding to the α-Na,K-ATPase MAB is a peptide wherein the 7 amino acid loop region of the MAB of α-Na,K-ATPase includes at least one conservative amino acid substitution which retains the amphipathic loop. The amphipathic loop in the α-NaK-ATPase MAB presents a hydrophobic face composed of two methionines and one phenylalanine, and a hydrophilic face composed of Glu-Ser-Lys-Asn on the opposite side. Accordingly, the amphipathic loop may be maintained in peptides of the following formula: $X_1X_2S\ F\ X_5X_6X_7$ (SEQ ID NO: 3); wherein $X_1$ is a nonpolar amino acid, preferably methionine or isoleucine; $X_2$ is a polar uncharged or negatively charged amino acid, preferably glutamic acid, aspartic acid, or serine; $X_5$ is a polar uncharged or positively charged amino acid, preferably lysine or asparagine; $X_6$ is a polar uncharged or positively charged amino acid, preferably lysine or asparagine; and $X_7$ is a nonpolar amino acid, preferably methionine or leucine. The polarity and charge characteristics of amino acids are commonly known.

Available amino acids which are not encoded by the genetic code may also be substituted for genetically encoded amino acids of the peptide of the invention.

The peptides of the present invention also include peptides wherein flanking sequence are added to produce or stabilize the peptides threedimensional structure. For instance, the peptides of the present invention include peptides containing the 7 amino acid loop region of the MAB of α-Na,K-ATPase flanked by amino acid sequences that promote the formation of a threeedimensional structure comprising the residue "loop" positioned on a "stalk" composed of anti-parallel β-strands.

Peptides of the invention include peptides that comprise the 5–7 amino acid loop region of the MAB, including peptides that are 5, 7, 8, 9, 10, 15, 20, 25, 26 or more amino acids in length.

Peptides of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

The peptides of the present invention can be provided alone, or in combination with other agents that modulate a particular pathological process. As used herein, two agents are said to be administered in combination when the two agents are administered simultaneously or are administered independently in a fashion such that the agents will act at the same time.

The peptides of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more peptides which modulate expression or at least one activity of a Na, K-ATPase. While individual needs vary, determination of optimal ranges of effective amounts of each component is within the skill of the art. Typical dosages comprise 0.1 to 100 μg/kg body wt. The preferred dosages comprise 0.1 to 10 μg/kg body wt. The most preferred dosages comprise 0.1 to 1 μg/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

The present invention further provides nucleic acid molecules that encode the peptides of the invention. Such nucleic acid molecules can be in an isolated form, or can be operably linked to expression control elements or vector sequences. The present invention further provides host cells that contain the vectors via transformation, transfection, electroporation or any other art recognized means of introducing a nucleic acid into a cell.

Another aspect of the present invention includes antibodies, including monoclonal antibodies and antibody fragments which retain binding to a MAB. The skilled artisan can use methods available in the art to produce antibodies against MABs (40).

Another aspect of the invention relates to a method of determining the minimal ankyrin binding domain and its three dimensional structure in other integral membrane proteins that associate or bind to ankyrin through the use of deletion analysis and carrier mediated crystallization.

The present invention also relates to a method of screening for compounds, including small peptides or peptide analogs, that inhibit, promote or modulate the interaction of a Na,K-ATPase and ankyrin. Similarly, the present invention contemplates the application of such screening techniques to other integral membrane proteins.

Lastly, the present invention relates to a method of inhibiting, promoting or modulating the interaction between a Na,K-ATPase and ankyrin in the presence of a compound, including small peptides or peptide analogs, that inhibits, promotes or modulates the interaction between a Na,K-ATPase and ankyrin

SPECIFIC EMBODIMENTS

Example 1
Identification of the Minimal Ankyrin Binding Domain (MAB) of α-Na,K-ATPase.

Figure 1:
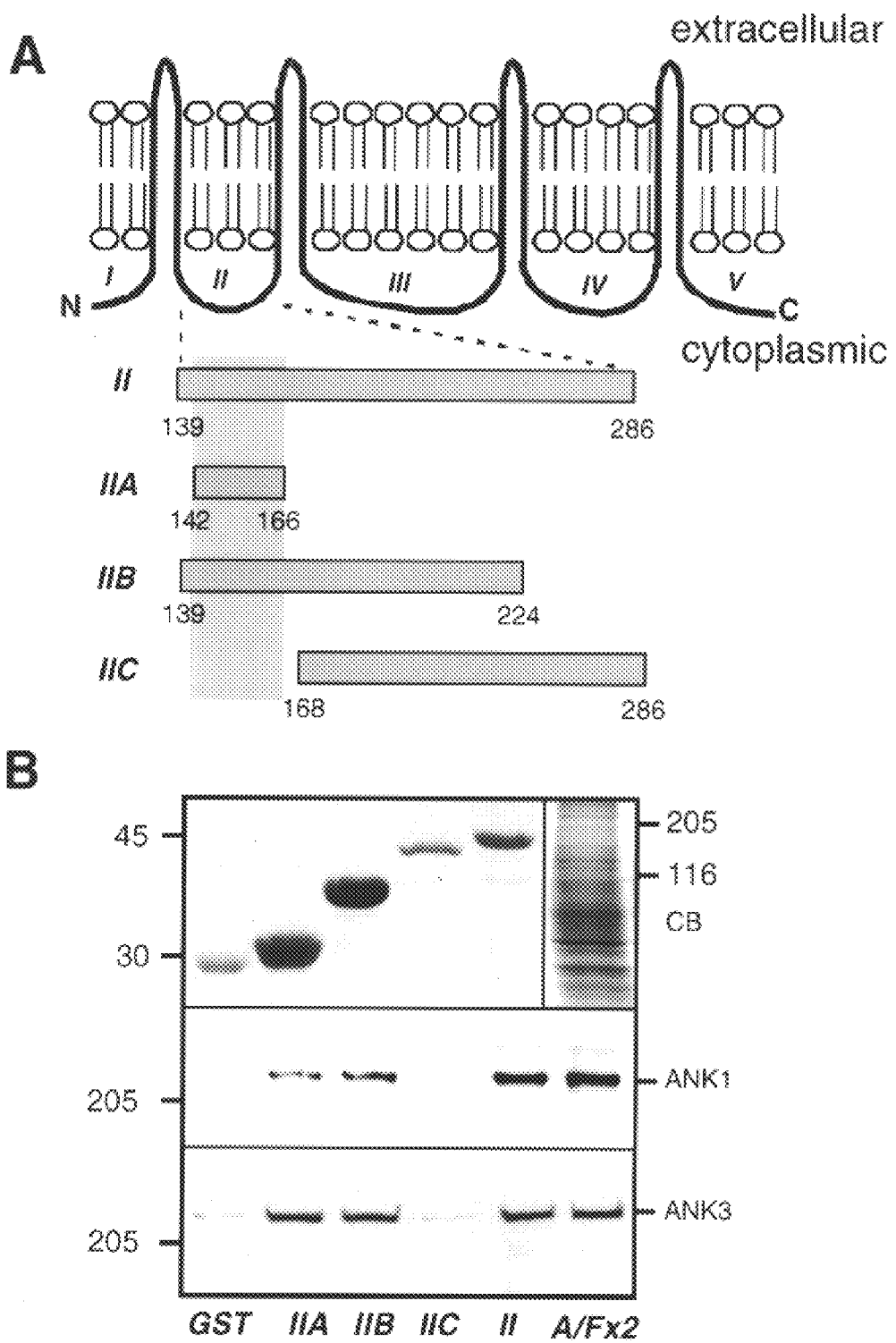

To elucidate the structural basis of the interaction between α-Na,K-ATPase and ankyrin, recombinant peptides derived from domain II of rat α-Na,K-ATPase were prepared as fusion peptides with glutathione-S-transferase (GST) and assayed in vitro for their ability to bind ANK1 (from red cells) or ANK3 (from Madin Darby Canine kidney cells) (FIG. 1). FIG. 1A is a schematic representation of the five cytoplasmic domains of α-Na,K-ATPase and their relationship to the ankyrin binding peptide sequences identified here. Codon positions defining each peptide are shown. Previous studies have established broad reactivity of cytoplasmic domains II and III with ankyrin, with domain II contributing most of the binding activity (29, 30).

For these experiments, a construct encoding domain II of α-Na,K-ATPase (29) was used as a template in a series of standard PCR amplifications. Oligonucleotides were targeted to amplify constructs IIa, IIb, and IIc. Amplification products were subcloned into TA vectors (Invitrogen), and sequenced by the dideoxynucleotide chain termination method (US Biochemical) to verify their identity. The constructs were then transferred into the pGEX-2T prokaryotic expression vector (Pharmacia) which directs the synthesis of foreign proteins as a fusion peptide with glutathione S-transferase (GST) in bacteria. Overnight cultures of transformed bacteria were induced with 0.5 mM isopropyl β-D-thiogalactoside, sonicated, centrifuged, and affinity purified on a 2-ml reduced glutathione-agarose column (29). GST alone was expressed as a control peptide. All peptides were eluted with 50 mM Tris-HCl, 5 mM reduced glutathione, pH 8.0, and dialyzed into ankyrin binding buffer (ABB: 50 mM Tris-HCl, pH 6.9/50 mM NaCl/1 mM DTT/1 mM EDTA/1 mM EGTA/1 mM PMSF/1 mM Pefabloc SC). Aliquots of peptides were analyzed by SDS/PAGE and Coomassie blue stained.

Each peptide (50 mg at 1 mg/ml) was conjugated to 50 ml of a 50% slurry of glutathione-agarose beads for 1 hr at 4° C. with gentle rotation for the binding assays. Ankyrin (ANK1) was isolated from human red blood cell ghosts and assayed for binding to fusion peptides by adding 25 mg of ankyrin to the conjugated beads; total volume was then brought to 500 ml with ABB, and after incubation overnight at 4° C. the bead fraction was analyzed by SDS-PAGE. Ankyrin was then detected by Western blotting with specific antibodies (29). Ankyrin (ANK3) was obtained from confluent MDCK cells extracted in situ to yield a high-salt extractable cytoskeletal fraction (Fx2) enriched for ankyrin (ANK3) (29). Conjugated beads were incubated with Fx2 (300 mg total protein) and bound ankyrin detected as above. All other procedures and the antibodies used for Western blotting were as before (7, 36).

In FIG. 1B, each peptide fusion construct with GST was examined for its ability to bind either purified ANK1 (from human red cells) or MDCK cell kidney ankyrin (ANK3) derived from whole MDCK cell lysates as above. Peptide IIA, with the sequence— SYYQEAKSSKIMESFKNMVPQQALV (SEQ ID NO: 2)-, is the minimal ankyrin binding domain identified in this experiment. Peptide IIa (residues 142–166 of α-Na,K-ATPase (numbered according to 31) retained full binding activity to both ANK1 and ANK3 isoforms, and constituted the minimal ankyrin binding domain (MAB) sequence. Domain II peptides not encompassing MAB, such as peptide IIc (residues 168–286), were devoid of ankyrin binding activity.

Three-dimensional Structure of the GST-MAB Peptide.

Attempts to crystallize the entire α-Na,K-ATPase domain II or MAB alone were not successful. Since the GST-MAB fusion peptide contained an ankyrin binding domain that was fully active, the method of carrier mediated crystallization was used to obtain structural information (32). The present invention encompasses the methods disclosed below of using GST as a carrier protein to successfully crystallize a peptide sequence heterologous to GST.

For this study the fusion peptide IIa was purified by HPLC gel-filtration chromatography into 50 mM Tris-HCl, pH 7.2, 150 mM NaCl, 2 mM β-mercaptoethanol. Crystals were prepared at RT by hanging-drop vapor diffusion against a reservoir of 30% polyethylene glycol 4000, 100 mM bis-tris-propane, 150 mM NaCl, 40 mM β-mercaptoethanol, pH 8.8, following previously described methods for carrier mediated crystallization (32). Diffraction data was collected with the R-AXISIIC imaging plate detector mounted on a Rigaku 200HM generator at −170° C. using a crystal flash frozen in crystallization buffer. Data was processed using the program DENZO and SCALEPACK (36), and was 86% complete (>2s). The structure was determined by molecular replacement using the published crystal structure of GST from *Schistosoma japonica* (33) and the program AMORE (37) of the CCP4 program suite (36). Successive rounds of model building and simulated annealing refinement were carried out with the program X-PLOR ver. 3.851 (38) and the CCP4 program suite. The graphic display program O version 5.10 (39) was used to build and correct the structure manually. Each residue of the final model was checked by the omit-map.

Figure 2:
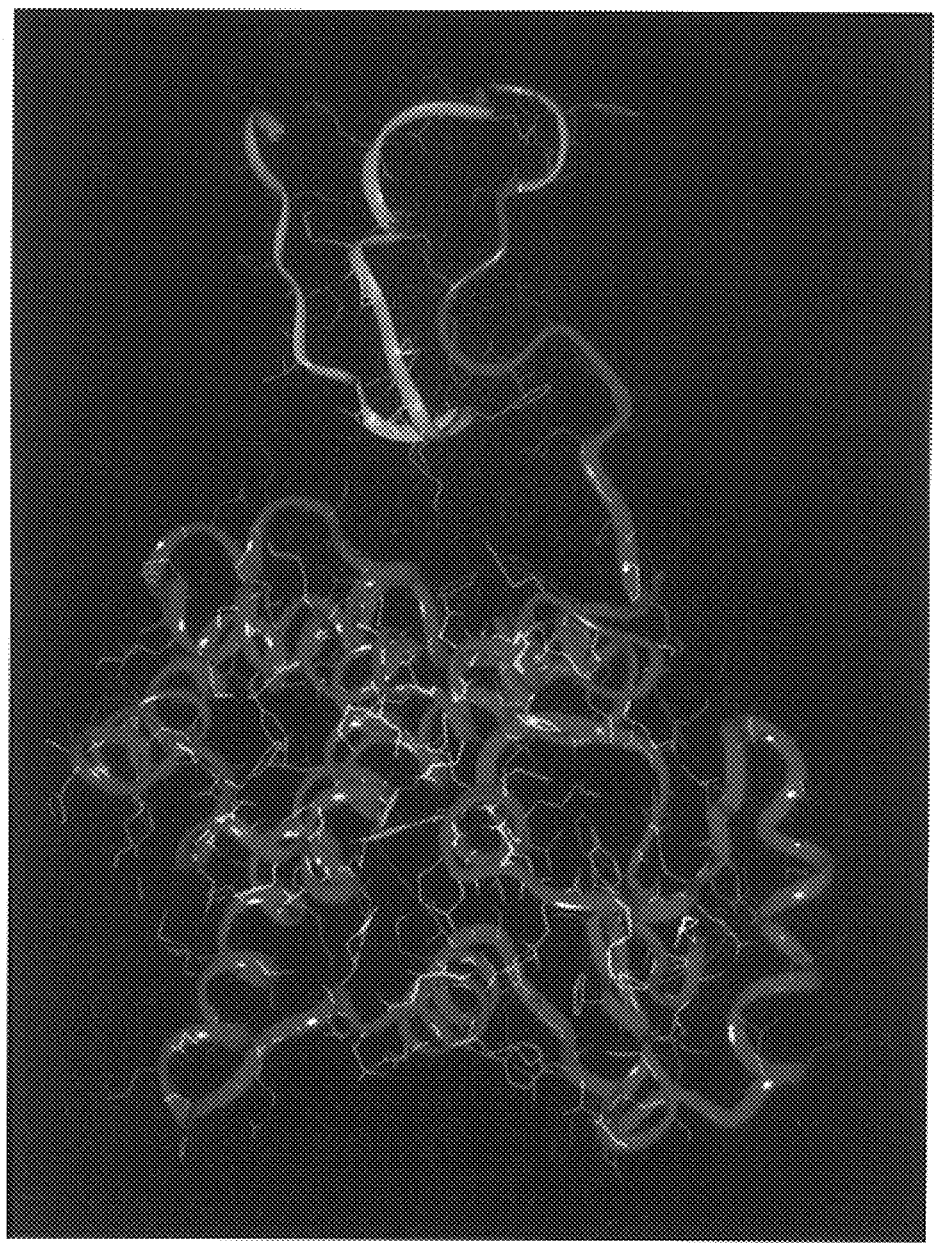

The active GST-fusion peptide containing MAB (construct IIA, FIG. 1, and FIG. 2) yielded ordered crystals (space group of P4(3)2(1)2, with a=b=92.17 and c=57.57). Diffraction of this crystal at −170° C. yielded a dataset that was 86% complete (>2s) and allowed the determination of the complete structure of the GST-MAB fusion peptide with an R-factor of 19.3 and free-R of 32.9 at 2.6 Å resolution (FIG. 2) using a molecular replacement strategy based on the known crystal structure of *Schistosoma japonicum* GST (SEQ ID NO: 4) (SjGST) (which has one molecule in the asymmetric unit and 41% solvent) (33). The refined model displayed a continuous main chain electron density and consisted of two domains, one representing SjGST and the other MAB (FIG. 2). Each residue of MAB was verified with an electron density omit-map.

Both the GST and MAB domains were well defined when the total structure was checked with the 2Fo-Fc map, including the side chains of $Leu_{118}$, $His_{215}$, and $Lys_{218}$, residues disordered in the published structure of SJGST (33). Backbone residues 1 to 210 of SjGST superimposed on those of SjGST-MAB with a RMS deviation of 1.02 Å. Differences between SjGST and SJGST-MAB were found in the position of $Met_1$, and the position of residues 211–218, which flank a region of disorder in SjGST (but not in SjGST-MAB). There were no discernible hydrophobic or salt interactions between GST and MAB. A single H-bond was detected between $Arg_{224}$ (residue 4 of the linker sequence) and $Gln_{248}$; (MAB, corresponding to $Gln_{163}$ in α-Na,K-ATPase); this bond does not alter the SjGST backbone conformation relative to SjGST alone. The three Gly residues (at 211, 212, 213) in GST, together with two Pro residues at 216 and 217 and the $Pro_{223}$-$Arg_{224}$-$Gly_{225}$-$Ser_{226}$ of the linker sequence (linker positions 3–6) collectively appear to well insulate MAB from secondary structural perturbations arising in SjGST.

The crystal structure of the fusion peptide thus displays two well separated and independently folded motifs, lending confidence that the structure of MAB as revealed in the fusion protein crystal is valid. Finally, it is clear from the graphical display that four MAB units are packed in each unit cell. Although theoretically the MAB conformation might be influenced by the packing force, these forces are usually quite small. Taken together, these considerations argue strongly that the conformation of MAB will not be influenced by the presence of SjGST, and that carrier mediated crystallization of active ankyrin-binding peptides fused with SjGST may represent an important and general approach to identifying the structural determinants of ankyrin binding activity in a variety or proteins.

Figure 3:
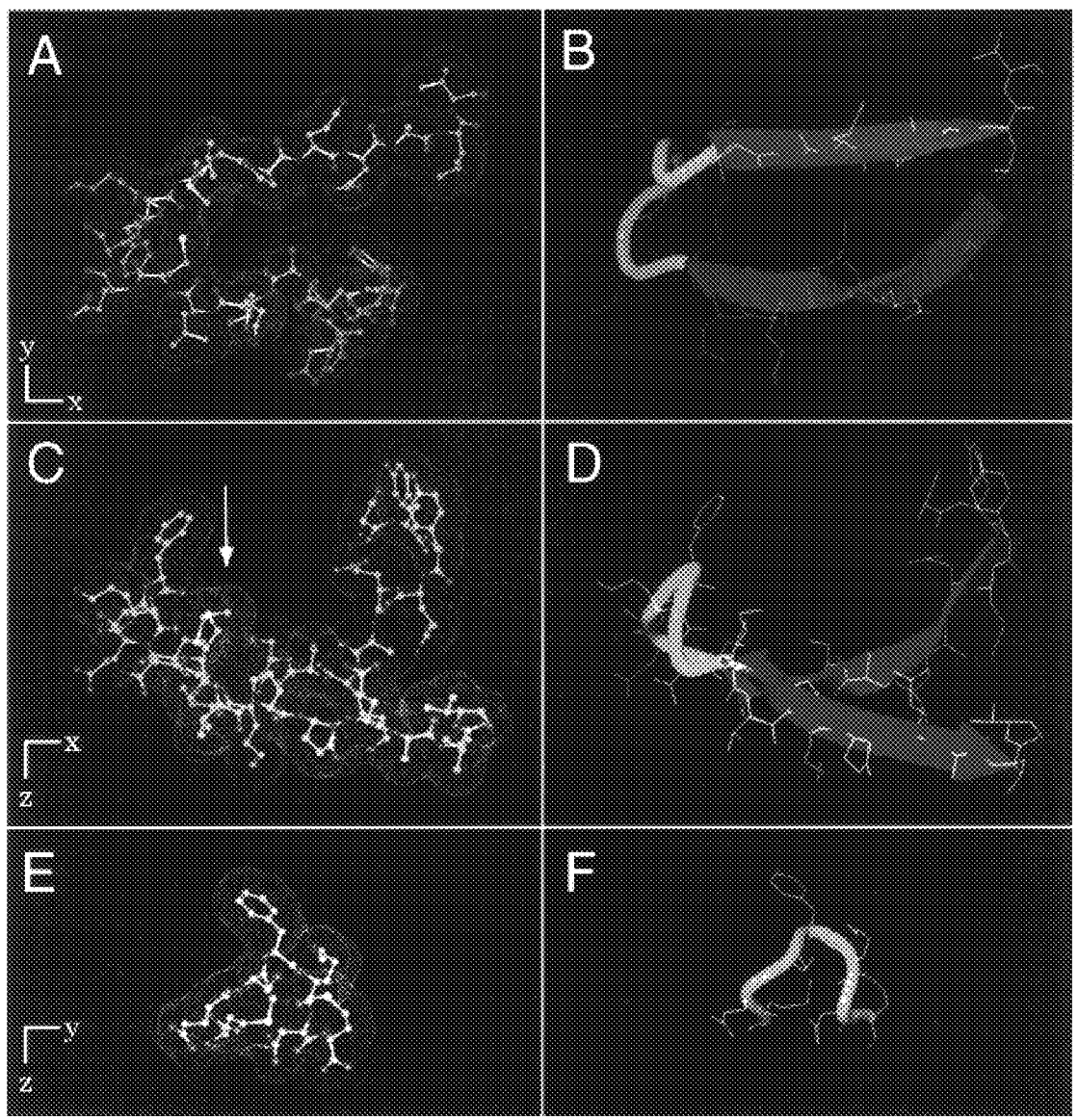

The overall three-dimensional structure of GST-M revealed two well-separated and folded domains. Detailed analysis of the ankyrin binding domain within SjGST-MAB reveals an antiparallel double β-strand flanking a loop composed of the seven residues-MESFKNM-(SEQ ID NO.1) (residues 152–158 of α-Na,K-ATPase) (FIG. 3). The overall structure of MAB is suggestive of a loop on a stalk. This loop is amphipathic, presenting a hydrophobic face composed of two methionines and one phenylalanine, and a hydrophilic face composed of Glu-Ser and Lys-Asn on the opposite side. A dipolar interaction between $Ser_{149}$ (position 234 in the crystal) and $Gln_{153}$ (crystal position 249) of the antiparallel β-strands stabilizes the stalk. Presumably, in intact α-NaK-ATPase, flanking sequences would further stabilize the stalk and probably alter the positioning of the terminal residues in MAB. A search of nucleotide and protein sequence banks (GenBank, Swiss-Prot) revealed exceptional conservation of MAB across species and between isoforms of α-NaK-ATPase (FIG. 4).

Sequences partially homologous to MAB also exist in gastric H,K-ATPase (48), which associates with ankyrin in gastric parietal cells (49). No homologous sequences were noted in other well-documented ankyrin binding proteins (including the erythrocyte anion exchanger, the amiloride-sensitive sodium channel, the voltage-sensitive sodium channel, the $Na^+/Ca^{++}$ exchanger, CD44, neurofascin, and IP3-R).

The foregoing structure of the ankyrin binding domain of α-NaK-ATPase was refined to an R-factor of 19.3 and free-R of 35.9 (4% of total data) at 2.6 Å resolution. The overall structure of GST is not significantly altered by the presence of the fusion construct, since superposition of SjGST onto that of SjGST-MAB yields a RMS deviation of 1.02 ø for backbone residues 1 to 210.

Three-axis Views of the Structure of the Minimal Ankyrin Binding Domain of α-Na,K-A TPase.

The basic structural motif is that of a seven residue "loop" on a "stalk" composed of antiparallel β-strands. FIGS. 3A, 3C and 3E are surface accessibility depictions showing the amphipathic surfaces formed by the "loop". FIGS. 3B, 3D and 3F are ribbon diagrams demonstrating the back-bone contour. It is envisioned that the seven residue loop interacts with the β-hairpin tips of one or more ankyrin repeat units (see FIG. 4). The arrow in FIG. 3C marks the depth of the structural place shown in FIGS. 3E and 3F).

Model of How Na,K-A TPases May Interact with One or More Ankyrin Repeat Units.

To determine the level of sequence homology among the ankyrin binding domains of different forms of Na,K-ATPase, the primary amino acid sequences of various ATPases were compared. A search of nucleotide and protein sequence banks (GenBank, Swiss-Prot) revealed that MAB is exceptionally well conserved across species and between isoforms of α-Na,K-ATPase (FIG. 4A). Sequences partially homologous to MAB also exist in gastric H,K-ATPase (34), which associates with ankyrin in gastric parietal cells (35). No homologous sequences were noted in other well-documented ankyrin binding proteins and their ankyrin binding sequences including the CD44, neurofascin, p53bp2 and IP3-R, However, like α-Na,K-ATPase, each of the other reported ankyrin binding sequences are short peptides.

FIG. 4B presents a model of how α-Na,K-ATPase may interact with ankyrin. While not being limited to the mechanism of interaction presented in this model, the model represents a possible scenario among others. Each ankyrin-repeat structure is composed of two alpha helices and a β-hairpin loop (5). Multiple repeat units create a structure in which interactions between the helices form a central core structure, while the tips of the exposed β-hairpin turns provide putative protein-protein interaction surfaces. In one scenario, the seven residue loop within MAB interacts with a specific site in ankyrin created by the tips of one or more of these β-hairpin turns. Since a multiplicity of potential binding pockets would be created by the 13 to 24 repeat units characteristic of most ankyrins, specific and unique binding sites presumably also exist for the other short peptide sequences responsible for ankyrin binding activity in other proteins. To effect this binding, we predict that these peptides will assume a "loop" on a "stalk" structural motif similar to that reported here for α-Na,K-ATPase.

These findings define the molecular structure of an integral membrane protein ankyrin-binding site, and provide significant insight into the mechanisms by which a variety of ligands may each interact specifically with ankyrin. Based on the crystal structure of p53bp2, each ankyrin-repeat is predicted to assume a novel L-shaped structure consisting of a β hairpin followed by two antiparallel helices (5). The plane of the β sheet is perpendicular to the helices, and the β-hairpin is mostly solvent exposed (FIG. 4). Multiple repeats form a core structure in which the alpha helices occupy the interior, and the structure is stabilized by a continuous anti-parallel β sheet formed between neighboring repeats and by extensive intra- and inter-repeat side chain hydrogen bonds.

A unique feature of this structure is the array of potential binding sites created by the protruding tips of the β-hairpin turns, either singly or in combination, and by the surfaces of the β-sheet formed between the protruding tips. Interestingly, these are the least conserved portions of the ankyrin repeat sequence, and thus offer the largest potential combinatorial complexity for interacting specifically with diverse ligands (in analogy to the variable region of antibody antigen recognition sites). It is possible that the seven residue loop and possibly portions of the β-stranded "stalk" of MAB interact specifically with these β-hairpin and sheet structures in the ankyrin repeat through interactions involving hydrophobic, H-bond, and ionic interactions (FIG. 4).

GST-MAB Binds Ankyrin with High Affinity.

Prior studies have detected Na,K-ATPase affinities for ankyrin in the range of 50 to 2600 mM (11,45,46). Of interest was whether GST-MAB bound ankyrin with comparable affinity. Purified ankyrin ($Ank_R$) was biotinylated, and its binding to GST-MAB or GST measured (FIG. 5). Non-linear regression analysis based on a bi-molecular binding model indicated that ankyrin specifically bound GST-MAB with a Kd=118±50 nM, in agreement with the affinity of intact Na,K-ATPase for ankyrin. Thus, while other regions of α-Na,K-ATPase such as the ALLK motif (SEQ ID NO: 6) identified in CD3 may contribute to its interaction with ankyrin (29,30), the 25 residues identified here are sufficient, and bind specifically to ankyrin but not to other proteins present in the whole kidney lysates (FIG. 1). GST alone was devoid of significant binding activity (FIG. 5). In separate studies we have also demonstrated that loss of these 25 residues in α-Na,K-ATPase abrogates its binding to ankyrin in vivo (47).

Given that the other reported ankyrin binding domains in CD44, IP3-R, and neurofascin are also small peptides, it is likely that while these sequences show no homology to MAB, they may also assume a "loop" on a "stalk" conformation that best enables them to interact with a unique complimentary site on the complex ankyrin surface. In that sense, the structure of MAB reported here may offer a glimpse into the general mechanism of how the profound multi-valency yet specificity of ankyrin is achieved. Finally, with the three-dimensional structure of MAB now in hand, and potentially a general approach for determining the structure of other short ankyrin binding sequences using deletional analysis and carrier mediated crystallization, it is now possible to design small molecule agents that block the interaction of specific macromolecules with ankyrin.

Example 2

The findings of Example 1 represent the first available data on the molecular structure of an integral membrane protein ankyrin-binding site, and provide significant insight into the mechanisms by which a variety of ligands may each interact specifically with ankyrin. The procedures used in to determine the MAB of the αNa,K-ATPase can be used as a general approach for determining the structure of other short ankyrin binding sequences.

As an example, the minimal ankyrin binding domain for other proteins that interact with ankyrin can be elucidated by the same methods of deletional analysis and carrier mediated crystallization. These proteins include, but are not limited to the erythrocyte anion exchanger, the amiloride-sensitive sodium channel, the voltage-sensitive sodium channel, the $Na^+/Ca^{++}$ exchanger, CD44, neurofascin, and IP3-R.

The first step of deletional analysis of a given protein comprises the construction of short fragments of the protein. The fragments are then tested for their ability to bind to ankyrin. Any procedure can be used to produce the short peptide fragments including, but not limited to, direct chemical synthesis of the peptides, direct cloning of DNA fragments that encode the peptide through the use of convenient restriction enzyme sites, as well as PCR amplification. For instance, a construct encoding the entire protein of interest or a domain of the protein is used as a template in a series of standard PCR amplifications (42). Oligonucleotides are designed to target and amplify constructs encoding the specific peptides desired. For proteins in which no domain of ankyrin interaction has not been identified, a series of overlapping peptides are produced that span the entire length of the protein or domain of interest, for instance a cytoplasmic domain of interest.

Amplification products are then be subcloned into expression vectors for direct expression of the encoded peptide or subcloned into vectors which produce fusion proteins amenable to standard purification techniques. For example, the amplification products are subcloned into TA vectors (Invitrogen), and sequenced by the dideoxynucleotide chain termination method (US Biochemical) to verify their identity. The constructs are then transferred into the pGEX-2T prokaryotic expression vector (Pharmacia) which directs the synthesis of foreign proteins as a fusion peptide with glutathione S-transferase (GST) in bacteria The fusion proteins are expressed and purified by standard techniques. As an example, overnight cultures of transformed bacteria are induced with 0.5 mM isopropyl β-D-thiogalactoside, sonicated, centrifuged, and affinity purified on a 2-ml reduced glutathione-agarose column (29). Peptides are then eluted with 50 mM Tris-HCl, 5 mM reduced glutathione, pH 8.0, and dialyzed into ankyrin binding buffer (ABB: 50 mM Tris-HCl, pH 6.9/50 mM NaCl/1 mM DTT/1 mM EDTA/1 mM EGTA/1 mM PMSF/1 mM Pefabloc SC). Aliquots of peptides are then analyzed by SDS/PAGE and Coomassie blue stained.

To determine the ability of the purified peptide to bind to ankyrin, any standard binding assay may be used (40, which is incorporated by reference in its entirety). For example, each peptide may be conjugated to a 50% slurry of glutathione-agarose beads for 1 hr at 4° C. with gentle rotation for the binding assays. Ankyrin (ANK1) is isolated from human red blood cell ghosts and assayed for binding to fusion peptides by adding 25 mg of ankyrin to the conjugated beads. After incubation overnight at 4° C. the bead fraction can be analyzed by SDS-PAGE and ankyrin detected by Western blotting with specific antibodies (29).

Peptides which are shown to bind to ankyrin are then crystallized to elucidate the three dimensional structure of the ankyrin binding site. Carrier mediated crystallization is then used as in Example 1 to determine the three-dimensional structure of the ankyrin binding site and is especially useful when determining the structure of small peptides or proteins no, amenable to direct crystallization.

Example 3

In general, several approaches can be used to identify an agent able to inhibit (block), enhance or in some other way modulate the interaction between an integral membrane protein or secretory protein and ankyrin This method may screen for compounds that disrupt, enhance or modulate the interaction of a specific integral membrane protein or a class of membrane or secretory proteins with homologous ankyrin binding.

The methods for determining whether a candidate compound inhibits, enhances or modulates the interaction between a protein such as the α-Na,K-ATPase and ankyrin can include any cell-free or cellular assay system. As an example of a cell-free system to detect compounds capable of inhibiting, enhancing or modulating the interaction between α-Na,K-ATPase, the MAB defined from α-Na,K-ATPase can be subcloned as a fusion peptide with glutathione S-transferase (GST) as in Example 1. The compound or agent to be tested is then contacted with the fusion protein in the presence of ankyrin. If the compound or agent inhibits, enhances or modulates in some way the interaction between α-Na,K-ATPase and ankyrin, the change in binding between α-Na,K-ATPase and ankyrin can be detected through standard techniques such as western blotting using anti-ankyrin antibodies. In this scenario, the fusion protein can be attached to a solid support such as glutathione-agarose beads. After incubation of the conjugated fusion protein with ankyrin and the compound or agent to be tested, the effect of the compound on binding can be tested by separating the bead fraction from the reaction mixture with subsequent detection of ankyrin binding using ankyrin specific antibodies (29).

As an example of a cellular assay system to detect the ability of a compound to inhibit, enhance or modulate the interaction between an integral membrane protein such as α-Na,K-ATPase and ankyrin, cells expressing both the α-NaK-ATPase and ankyrin can be contacted (incubated) with the compound and the intracellular transport of the protein such as α-Na,K-ATPase measured. If the compound is capable of inhibiting or enhancing the interaction between α-Na,K-ATPase and ankyrin, the transport of α-Na,K-ATPase to the plasma membrane and/or transport from the endoplasmic reticulum to the Golgi apparatus will be disrupted or enhanced. This can be detected by the use of antibodies that bind specifically to α-Na,K-ATPase or through functional assays that detect the presence of the Na,K-ATPase on the plasma membrane.

It should be understood that the foregoing discussion and examples merely present a detailed description of certain preferred embodiments. It therefore should be apparent to those of ordinary skill in the art that various modifications and equivalents can be made without departing from the spirit and scope of the invention. All articles and texts that are identified above are incorporated by reference in their entirety.

References

The following references are hereby incorporated by reference in their entirety:

REFERENCES

1. A. W. Ferrante, Jr., R. Reinke, E. R. Stanley, *Proc Natl Acad Sci USA* 92, 911–5 (1995).
2. R. J. Diederich, K. Matsuno, H. Hing, T. S. Artavanis, *Development* 120, 473–81 (1994).
3. M. E. Fortini, I. Rebay, L. A. Caron, T. S. Artavanis, *Nature* 365, 555–7 (1993).
4. H. Zhang, D. C. Scheirer, W. H. Fowle, H. M. Goodman, *Plant Cell* 4, 1575–88 (1992).
5. S. Gorina, N. P. Pavletich, *Science* 274, 1001–5 (1996).
6. K. Beck, J. A. Buchanan, W. J. Nelson, *In revision* (1997).
7. P. Devarajan, et al., *Journal Cell Biology* 133, 819–830 (1996).
8. Devarajan, P., Stabach, P. R., De Matteis, M. A. and Morrow, J. S. (1997) *Proc. Natl. Acad. Sci (USA)* 94, 10711–6.
9. A. Godi, et al., submitted (1997).
10. W. J. Nelson, R. W. Hammerton, A. Z. Wang, E. M. Shore, *Seminars in Cell Biology* 1, 359–371 (1990).
11. D. Gundersen, J. Orlowski, B. E. Rodriguez, *J Cell Biol* 112, 863–72 (1991).
12. J. S. Morrow, C. Cianci, T. Ardito, A. Mann, M. T. Kashgarian, *J. Cell Biol.* 108, 455–465 (1989).
13. P. Devarajan, J. S. Morrow, in *Membrane Protein-Cytoskeleton Complexes: Protein Interactions, Distributions and Functions* W. J. Nelson, Ed. (Academic Press, New York, 1996), vol. 43, pp. 97–128.
14. J. Q. Davis, T. McLaughlin, V. Bennett, *J Cell Biol* 121, 121–33 (1993).
15. V. B. Lokeshwar, N. Fregien, L. Y. Bourguignon, *J Cell Biol* 126, 1099–109 (1994).
16. T. Leveillard, I. M. Verma, *Gene Expr* 3, 135–50 (1993).
17. I. Rebay, R. G. Fehon, T. S. Artavanis, *Cell* 74, 319–29 (1993).
18. L. Y. Bourguignon, V. B. Lokeshwar, X. Chen, W. G. Kerrik, *J Immunol* 151, 6634–44 (1993).
19. L. Y. Bourguignon, H. Jin, *J Biol Chem* 270, 7257–60 (1995).
20. C. C. Gregorio, E. A. Repasky, V. M. Fowler, J. D. Black, *J Cell Biol* 125, 345–58 (1994).
21. L. D. Kerr, J. Inoue, I. M. Verma, *Curr Opin Cell Biol* 4, 496–501 (1992).
22. J. Inoue, T. Takahara, T. Akizawa, O. Hino, *Oncogene* 8, 2067–73 (1993).
23. V. Bennett, *J Biol Chem* 267, 8703–6 (1992).
24. J. S. Morrow, et al., in *Handbook of Physiology* J. Hoffman, J. Jamieson, Eds. (Oxford, London, 1997), vol. chapter II, pp. 485–540.
25. E. J. Luna, A. L. Hitt, *Science* 258, 955–964 (1992).
26. V. Bennett, D. M. Gilligan, *Annu Rev Cell Biol* 9, 27–66 (1993).
27. P. Michaely, V. Bennett, *J Biol Chem* 268, 22703–9 (1993).
28. P. Michaely, V. Bennett, *Trends Cell Biol.* 2, 127 (1992).
29. P. Devarajan, D. A. Scaramuzzino, J. S. Morrow, *Proceedings of the National Academy of Science (USA)* 91, 2965–2969 (1994).
30. C. Jordan, B. Puschel, R. Koob, D. Drenckhahn, *Journal Biological Chemistry* 270, 29971–29975 (1995).
31. G. E. Shull, J. Greeb, J. B. Lingrel, *Biochemistry* 25, 8125–8132 (1986).
32. J. P. Donaghue, H. Patel, W. F. Anderson, J. Hawiger, *Proceedings of the National Academy of Science (USA)* 91, 12178–12182 (1994).
33. C. A. McTigue, D. R. Williams, J. A. Tainer, *Journal of Molecular Biology* 246, 21–27 (1995).
34. G. E. Shull, J. B. Lingrel, *J Biol Chem* 261, 16788–91 (1986).
35. P. R Smith, et al., *Am J Physiol* 264, C63–70 (1993).
36. Z. Otwinoski, Proceedings of the CCP4 Study weekend, L. Sawyer et al. Eds (1993).
37. J. Navaza, *Acta Cryst.* A50, 157–163 (1994).
38. A. T. Brünger, (Yale University Press, New Haven, 1992).
39. T. A. Jones, M. Kjeldgaard, Uppsala University, Sweden and Aarhus University, Denmark (1996)

40. Harlow and Lane, Antibodies: a laboratory manual, Cold Spring Harbor Pubs, N.Y. (1988).
41. Ausbel et al., Current Protocols in Molecular Biology, Greene Publishing and Wiley-Interscience, N.Y. (1987).
42. Innis, M. et al., PCR Protocols: a guide to methods and applications, Academic Press, San Diego (1990).
43. Sambrook et al., Molecular Cloning: a laboratory manual (2nd Ed.), Vol.1–3. Cold Spring Harbor Laboratory (1989).
44. Scopes, Protein Purification: principles and practice, Springer-Verlag, N.Y. (1982).
45. Davis, J. Q. and Bennett, V. (1990) *J Biol Chem* 265, 17252–6.
46. Nelson, W. J. and Veshnock, P. J. (1987) *Nature* 328, 533–536.
47. Devarajan, P., Stabach, P. R., Liu, M. and Morrow, J. S. (1997) *Molec.Biol.Cell* 8 (supp), 305a.
48. Shull, G. E. and Lingrel, J. B. (1986) *J Biol Chem* 261, 16788–91.
49. Smith, P. R., Bradford, A. L., Joe, E. H., Angelides, K. J., Benos, D. J. and Saccomani, G. (1993) *Am J Physiol* 264, C63–70.

What is claimed is:

1. An isolated peptide of 8, 9, 10, 15, 20, 25 or 26 amino acid residues comprising the minimal ankyrin binding domain amino acid sequence of SEQ ID NO: 1.

2. The isolated peptide of claim 1, wherein the amino acid sequence comprises SEQ ID NO: 2.

3. An isolated peptide of 8, 9, 10, 15, 20, 25 or 26 amino acid residues comprising the minimal ankyrin binding domain amino acid sequence $X_1 X_2$ Ser Phe $X_5 X_6 X_7$ (SEQ ID NO: 3) wherein:
   (a) $X_1$ is a nonpolar amino acid selected from the group consisting of methionine and isoleucine;
   (b) $X_2$ is a polar uncharged or negatively charged amino acid, selected from the group consisting of glutamic acid, aspartic acid and serine;
   (c) $X_5$ and $X_6$ are either polar uncharged or positively charged amino acids selected from the group consisting of lysine and asparagine;
   (d) $X_7$ is a nonpolar amino acid selected from the group consisting of methionine and leucine.

4. A fusion peptide comprising any one of the isolated peptides of claims 1, 2 or 3 and a second peptide.

5. The fusion peptide of claim 4 wherein the second peptide is glutathione-S-transferase.

6. An isolated peptide comprising the amino acid sequence of SEQ ID NO: 1 which blocks the activity of alpha-Na,K ATPase by modulating the binding of alpha-Na,K ATPase to ankyrin.

7. The isolated peptide of claim 6, wherein the amino acid sequence comprises SEQ ID NO: 2.

8. The isolated peptide of claim 6, wherein the binding of alpha-Na,K ATPase to ankyrin is inhibited.

9. The isolated peptide of claim 8, wherein the inhibition of binding blocks transport of alpha-Na,K ATPase to the plasma membrane.

10. An isolated peptide which blocks the activity of alpha-Na,K ATPase by modulating the binding of the alpha-Na,K ATPase to ankyrin comprising the sequence $X_1 X_2$ Ser Phe $X_5 X_6 X_7$ (SEQ ID NO: 3) wherein:
   (a) $X_2$ is a nonpolar amino acid selected from the group consisting of methionine and isoleucine;
   (b) $X_2$ is a polar uncharged or negatively charged amino acid, selected from the group consisting of glutamic acid, aspartic acid and serine;
   (c) $X_5$ and $X_6$ are either polar uncharged or positively charged amino acids selected from the group consisting of lysine and asparagine;
   (d) $X_7$ is a nonpolar amino acid selected from the group consisting of methionine and leucine.

11. The isolated peptide of claim 10, wherein the amino acid sequence comprises SEQ ID NO: 1.

12. The isolated peptide of claim 11, wherein the amino acid sequence comprises SEQ ID NO: 2.

13. The isolated peptide of claim 10, wherein the binding of alpha-Na,K ATPase to ankyrin is inhibited.

14. The isolated peptide of claim 13, wherein the inhibition of binding blocks transport of alpha-Na,K ATPase to the plasma membrane.

15. A fusion peptide comprising any one of the isolated peptides of claim 6 or 10 and a second peptide.

16. The fusion peptide of claim 15 wherein the second peptide is glutathione-S-transferase.

17. An isolated peptide consisting of SEQ ID NO: 1.

18. An isolated peptide consisting of SEQ ID NO: 2.

* * * * *